United States Patent [19]

Sano et al.

[11] 4,346,170
[45] Aug. 24, 1982

[54] METHOD FOR PRODUCING L-LYSINE BY FERMENTATION

[75] Inventors: Kounosuke Sano, Tokyo; Takayasu Tsuchida, Kawasaki, both of Japan

[73] Assignee: Ajinomoto Company, Incorporated, Tokyo, Japan

[21] Appl. No.: 171,317

[22] Filed: Jul. 23, 1980

[30] Foreign Application Priority Data

Jul. 23, 1979 [JP] Japan .................................. 54-93533

[51] Int. Cl.³ ...................... C12P 13/08; C12N 15/00; C12N 1/20; C12N 1/00
[52] U.S. Cl. ...................................... 435/115; 435/68; 435/172; 435/253; 435/317; 435/849
[58] Field of Search ................. 435/115, 172, 253, 317

[56] References Cited

U.S. PATENT DOCUMENTS

| | | | |
|---|---|---|---|
| 3,871,960 | 3/1975 | Kubota et al. | 435/115 |
| 3,905,866 | 9/1975 | Watanabe et al. | 435/115 |
| 4,066,501 | 1/1978 | Tosaka et al. | 435/172 |
| 4,169,763 | 10/1979 | Nakayama et al. | 435/115 |
| 4,237,224 | 12/1980 | Cohen et al. | 435/172 |
| 4,278,765 | 7/1981 | Debabov et al. | 435/115 |

OTHER PUBLICATIONS

Shive et al., in *Metabolic Inhibitors, A comprehensive Treatise,* (1963), Hochster et al. (ed.), Academic Press, New York, vol. 1, pp. 1–4, 22–23.

*Primary Examiner*—Alvin E. Tanenholtz
*Assistant Examiner*—J. Martinell
*Attorney, Agent, or Firm*—Oblon, Fisher, Spivak, McClelland & Maier

[57] ABSTRACT

An L-lysine producing microorganism which is obtained by incorporation into a host strain of the genus Escherichia of a hybrid plasmid having inserted therein a DNA fragment with genetic information controlling L-lysine production which is derived from a donor strain which is resistant to an L-lysine analogue, is useful for the production of high levels of L-lysine by fermentation.

17 Claims, No Drawings

METHOD FOR PRODUCING L-LYSINE BY FERMENTATION

BACKGROUND OF THE INVENTION

1. Field of the Invention

The present invention relates to a method for producing L-lysine by fermentation, and particularly relates to a method for producing L-lysine with a microorganism constructed by a gene recombination technique.

2. Description of the Prior Art

Hitherto, in order to render a wild strain capable of producing L-lysine from carbohydrates, it has been necessary to induce artificial mutants from the wild strain. There are many known lysine-producing artificial mutants. Most of the known lysine-producing mutants are resistant to lysine-analogues such as S-(2-aminoethyl)-cysteine (AEC), and/or require homoserine for growth, and belong to the genus Brevibacterium or Corynebacterium. These microorganisms produce L-lysine in a yield of from 40 to 50%. Examples of recent publications concerning L-lysine production by fermentation are: Japanese Published Unexamined Patent Application Nos. 9784/1980, 9783/1980, 9559/1980, 9785/1980, 86091/1978, 86090/1978, 86089/1978, 26391/1978, 20490/1978, 9394/1978 and 6486/1978.

It has however, become difficult to increase the yields of L-lysine using the artificial mutation techniques. A need therefore, continues to exist for the development of novel microorganisms capable of producing L-lysine in high yields.

SUMMARY OF THE INVENTION

It is therefore an object of the invention to provide for a novel microorganism capable of producing high yields of L-lysine.

Another object of the invention is to provide a method for producing L-lysine in high yields.

These and other objects of the invention, which will hereinafter become more readily apparent have been attained by providing:

an L-lysine producing microorganism which is obtained by incorporating into a host strain of the genus Escherichia, a hybrid plasmid having inserted therein a DNA fragment with genetic information controlling L-lysine production which is derived from a donor strain which is resistant to an L-lysine analogue.

Another object of the invention has been attained by providing a hybrid plasmid derived by inserting into a plasmid selected from the group consisting of Col E1, pSC 101, pBR 322, pACYC 177, pCR 1, R6K and λ phage, a DNA fragment containing information controlling L-lysine production, which DNA fragment is derived from the DNA of a donor strain which is resistant to an L-lysine analogue.

Another object of the invention has been attained by providing a method for producing L-lysine which comprises:

culturing in a culture medium an L-lysine producing microorganism which is obtained by incorporating into a host strain of the genus Escherichia, a hybrid plasmid having inserted therein a DNA fragment with genetic information controlling L-lysine production which is derived from a donor strain which is resistant to an L-lysine analogue and recovering the L-lysine accumulated in the culture medium.

DETAILED DESCRIPTION OF THE PREFERRED EMBODIMENTS

The inventors have succeeded in obtaining an L-lysine producing microorganism of the genus Escherichia, which produces L-lysine in a yield higher than artificially induced mutants of Escherichia.

This microorganism has therefore also provided a method for producing L-lysine by fermentation, which comprises: culturing in a culture medium an L-lysine producing microorganism constructed by incorporating a hybrid plasmid in a recipient of the genus Escherichia and recovering the L-lysine accumulated in the culture medium, said hybrid plasmid containing a deoxyribonucliec acid fragment possessing genetic information related to L-lysine production and obtained from a microorganism of the genus Escherichia resistant to a lysine-analogue.

The DNA-donor strain used to construct the L-lysine producer of this invention is a microorganism of the genus Escherichia possessing genetic information related to L-lysine production. Strains having higher productivity of L-lysine are used preferably as the DNA-donor. The mutant resistant to the lysine-analogue used as the DNA-donor can be obtained by conventional mutation techniques.

The lysine-analogues are those which inhibit the growth of Escherichia strains, but the inhibition is suppressed partially or completely when L-lysine coexists in the medium. Examples of lysine-analogues are oxo-lysine, lysine-hydroxamate, AEC, γ-methyl-lysine, and β-chloro-caprolactam.

Chromosomal DNA is extracted from the DNA donor in a well known manner and treated with a restriction endonuclease by a well known method (Biochem. Biophys. Acta 383: 457 (1975)).

The plasmid or phage DNA used as the vector in the synthesis procedure is also treated with a restriction endonuclease in an analogous manner. Various kinds of restriction endonucleases can be used, if the digestion of the chromosomal DNA is done partially. Thereafter, the digested chromosomal DNA and vector DNA are subjected to a ligation reaction.

Recombination of DNA to prepare the recombinant plasmid can be carried out by incorporating with terminal transferase deoxyadenylic acid and thymidylic acid, or deoxyguanylic acid and deoxycytidylic acid into the chromosomal DNA fragment and cleaved vector DNA, and by subjecting the modified chromosomal DNA fragment and cleaved DNA to an annealing reaction.

As a suitable vector DNA, a conventional vector can be employed such as Col E1, pSC 101, pBR 322, pACYC 177, pCR 1, R6K, or λ-phage, or their derivatives.

The hybrid DNA thus obtained can be incorporated into a microorganism of the genus Escherichia by conventional transformation techniques, J. Bacteriol., 119: 1072 (1974). The desired transformant is screened using a medium on which only a clone, having one or both of the characteristics of L-lysine productivity possessed by the chromosomal DNA fragment and those possessed by vector DNA, can grow.

As the recipient microorganism for the hybrid DNA, an L-lysine-auxotroph is usually used, since it is conventional to distinguish the lysine-producing transformant from the recipient. Desirably, a mutant already having higher productivity of L-lysine is used as the recipient, to obtain better results.

The methods of culturing the L-lysine producing strains thus obtained are conventional, and are similar to the methods for the cultivation of known L-lysine producing microorganisms. Thus, the culture medium employed is a conventional one containing carbon sources, nitrogen sources, inorganic ions and, when required, minor organic nutrients such as vitamins or amino acids. Examples of suitable carbon sources include glucose, sucrose, lactose, starch hydrolysate and molasses. Gaseous ammonia, aqueous ammonia and ammonium salts and other nitrogen containing materials can be used as the nitrogen source.

Cultivation of the recombinant microorganisms is conducted under aerobic conditions in which the pH and the temperature of the medium are adjusted to a suitable level and continued until the formation of L-lysine ceases.

The L-lysine accumulated in the culture medium can be recovered by conventional procedures.

By the method of the present invention, L-lysine can be produced in higher yields than has been achieved in previously known methods using artificial mutants of Escherichia.

Having generally described this invention, a further understanding can be obtained by reference to certain specific examples which are provided herein for purposes of illustration only and are not intended to be limiting unless otherwise specified.

EXAMPLE 1

(1) Preparation of chromosomal DNA possessing genetic information related to L-lysine production.

*Escherichia coli* EL-1, NRRL B-12199 a mutant resistant to AEC, and derived from K-12 (ATCC 10798) by exposing K-12 cells to 250 μg/ml of N-methyl-N'-nitro-N-nitrosoguanidine in a citric acid buffer of pH 6.0 at 30° C. for 60 minutes, and separating the colony which appeared on the agar medium, was cultured at 37° C. for 3 hours with shaking in 1 l of L-medium containing 1 g/dl peptone, 0.5 g/dl yeast extract, 0.1 g/dl glucose and 0.5 g/dl NaCl (pH was adjusted to 7.2), and bacterial cells in the exponential growth phase were harvested. Chromosomal DNA was extracted by a conventional phenol-method, and 3.6 mg of purified DNA was obtained.

(2) Preparation of vector DNA

As the vector, DNA of Col El was prepared as follows:

A strain of *Escherichia coli* K-12 harboring the plasmid Col El was incubated at 37° C. in 1 l of a glucose-"casamino acid"-inorganic salts medium containing: 2 g glucose, 1 g NH$_4$Cl, 6 g Na$_2$HPO$_4$, 3 g KH$_2$PO$_4$, 5 g NaCl, 0.1 g MgSO$_4$.7H$_2$O, 0.015 g CaCl$_2$.2H$_2$O, 20 g "casamino acid", 0.05 g thymine, 0.05 g L-methionine and 100 μg thiamine HCl per liter (pH was adjusted to 7.2). After the strain was incubated until the late log phase, 170 μg/ml of chloramphenicol was added to the culture medium. Through this process, the plasmid DNA was amplified and accumulated abundantly in the bacterial cells.

After 16 hours of the incubation, cells were harvested and then lysed by treatment with lysozyme and SDS. The lysate was centrifuged at 30,000 xg for 1 hour to obtain the supernatant. After concentrating the supernatant, 450 μg of the plasmid DNA was obtained by fractionation using cesium chloride-ethidium bromide equilibrium density gradient centrifugation.

(3) Insertion of chromosomal DNA fragment into vector.

10 μg of the chromosomal DNA was treated with the restriction endonuclease EcoRI at 37° C. for 5, 10, 20, 30 and 60 minutes, respectively, to cleave the DNA chains, and then heated at 65° C. for 5 minutes, respectively. 10 μg of the vector DNA was also treated with the restriction endonuclease EcoRI at 37° C. for 1 hour to cleave the DNA completely, and then heated at 65° C. for 5 minutes.

The digested chromosomal DNA solution and cleaved vector DNA solution were mixed and subjected to the ligation reaction of DNA fragments by the T$_4$ phage DNA-ligase in the presence of ATP and dithiothreitol at 10° C. for 24 hours. The reaction mixture was then heated at 65° C. for 5 minutes, and two folds volume of ethanol was added to it. The precipitated recombinant DNA was recovered.

(4) Genetic transformation with the hybrid plasmid harboring the genetic information related to L-lysine production.

A biotin and thymine requiring strain, *Escherichia coli* BT-14, NRRL B-12200 which was derived from *Escherichia coli* K-12 by N-methyl-N'-nitro-N-nitrosoguanidine mutagenesis, (250 μg/ml in a citric acid buffer, pH 6.0 at 30° C. for 60 minutes, and separated as the biotin, thiamine requiring mutant) was cultured in 10 ml of L-medium at 37° C. with shaking. Cells in exponential growth phase were harvested, and suspended in 0.1 M MgCl$_2$ solution and then in 0.1 M CaCl$_2$ solution in an ice-bath, whereby "competent" cells having the ability of DNA uptake were prepared.

Into the competent cells suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes, the cells, thus being incorporated with the hybrid plasmid DNA, were inoculated into L-medium and the medium was shaken at 37° C. for 3 hours, whereby the transformation reaction was completed. The cells were harvested, washed, and resuspended. A small portion of the cells suspension was spread on an agar plate containing, 2 g glucose, 1 g(NH$_4$)$_2$SO$_4$, 7 g K$_2$HPO$_4$, 2 g KH$_2$PO$_4$, 0.1 g MgSO$_4$.7H$_2$O, 0.5 sodium citrate.2H$_2$O, 1 g AEC.HCl, biotin 0.1 mg, thiamine.HCl 0.1 mg, and 2 g agar, per liter, (pH was adjusted to 7.2). The plate was incubated at 37° C. for 3 days.

Colonies appearing on the plate were picked up and L-lysine-producing transformants were selected by the formation of halo on a minimum-agar-medium on which lysine requiring mutant L-1 induced from *Escherichia coli* K-12 had previously been spread.

Thus, AJ 11442, FERM-P 5084, NRRL B-12185 was obtained as the lysine-producing transformant.

(5) Production of L-lysine by the novel L-lysine-producing strain.

Table 1 shows the experimental result of the fermentative production of L-lysine using the strains NRRL B-12185 and the DNA-donor strain EL-1, an artificial mutant.

The fermentation medium contained 5 g/dl glucose, 2.5 g/dl ammonium sulfate, 0.2 g KH$_2$PO$_4$, 0.1 g/dl MgSO$_4$.7H$_2$O, 0.05 g/dl yeast extract, 100 μg/dl thiamine.HCl, 30 μg/dl biotin, 1 mg/dl FeSO$_4$.7H$_2$O, 1 mg/dl MnSO$_4$.4H$_2$O and 2.5 g/dl CaCO$_3$ (separately sterilized) and the pH was adjusted to 7.0.

Twenty ml batches of the fermentation medium was placed in 500 ml flasks, inoculated with one loopful inoculum of the test microorganism, and the cultivation was carried out at 31° C. for 72 hours.

The amount of L-lysine in the supernatant of the fermentation broth was determined by microbiological assay.

| Microorganism tested | L-lysine produced (mg/dl) |
|---|---|
| EL-1 | 16 |
| NRRL B-12185 | 28 |

What is claimed as new and intended to be covered by Letters Patent of the United States is:

1. An L-lysine producing organism which is obtained by incorporation into a host strain of the genus Escherichia of a hybrid vector having inserted therein a DNA fragment with genetic information controlling L-lysine production, which fragment is derived from a donor strain of the genus Escherichia which is resistant to an L-lysine analogue.

2. The microorganism of claim 1, wherein said host strain is *Escherichia coli* BT-14, NRRL B-12200.

3. The microorganism of claim 1, wherein said donor strain is *Escherichia coli* EL-1, NRRL B-12199.

4. The microorganism of claim 1, wherein said donor strain is resistant to an analogue selected from the group consisting of oxo-lysine, lysine-hydroxamate, S-(2-aminoethyl)-cysteine, γ-methyl-lysine, and β-chloro-caprolactam.

5. The microorganism of claim 1, which is *Eschericha coli* NRRL B-12185.

6. The microorganism of claim 1, wherein said hybrid vector is derived from a member selected from the group consisting of Col E1, pSC 101, pBR 322, pACYC 177, pCR 1, R6K and γ phage.

7. The microorganism of claim 1, wherein said vector is derived from Col E1.

8. A hybrid vector derived from insertion into a vector selected from the group consisting of Col E1, pSC 101, pBR 322, pACYC 177, pCR 1, R6K and γ phage, of a DNA fragment containing information controlling L-lysine production, which DNA fragment is derived from the DNA of a donor strain of the genus Escherichia which is resistant to an L-lysine analogue.

9. The vector of claim 8, which is derived from Col E1.

10. The vector of claim 8, wherein said donor strain is *Escherichia coli* EL-1, NRRL 12199.

11. A method of producing L-lysine which comprises culturing in a culture medium an L-lysine producing microorganism which is obtained by incorporation into a host strain of the genus Escherichia, of a hybrid vector having inserted therein a DNA fragment with genetic information controlling L-lysine production which fragment is derived from a donor strain of the genus Escherichia which is resistant to an L-lysine analogue, and recovering the L-lysine accumulated in the culture medium.

12. The method of claim 11, wherein said host strain is *Escherichia coli* BT-14, NRRL B-12200.

13. The method of claim 11, wherein said donor strain is *Escherichia coli* EL-1, NRRL B-12199.

14. The method of claim 11, wherein said donor strain is resistant to an analogue selected from the group consisting of oxo-lysine, lysine-hydroxamate, S-(2-aminoethyl)-cysteine, γ-methy-lysine and β-chloro-caprolactam.

15. The method of claim 11, wherein said L-lysine producing microorganism is *Escherichia coli* NRRL B-12185.

16. The method of claim 11, wherein said hybrid vector is derived from a member selected from the group consisting of Col E1, pSC 101, pBR 322, pACYC 177, pCR 1, R6K and λ phage.

17. The method of claim 11, wherein said vector is derived from Col E1.

* * * * *